US009222872B2

(12) United States Patent
Buchanan et al.

(10) Patent No.: US 9,222,872 B2
(45) Date of Patent: Dec. 29, 2015

(54) FLOW CYTOMETER NOZZLE TIP

(71) Applicant: INGURAN, LLC, Navasota, TX (US)

(72) Inventors: Kris Buchanan, Fort Collins, CO (US);
Kenneth Michael Evans, College Station, TX (US)

(73) Assignee: Inguran, LLC, Navasota, TX (US)

(*) Notice: Subject to any disclaimer, the term of this patent is extended or adjusted under 35 U.S.C. 154(b) by 53 days.

(21) Appl. No.: 14/032,086

(22) Filed: Sep. 19, 2013

(65) Prior Publication Data
US 2014/0078502 A1 Mar. 20, 2014

Related U.S. Application Data

(63) Continuation-in-part of application No. PCT/US2013/031787, filed on Mar. 14, 2013.

(60) Provisional application No. 61/842,310, filed on Jul. 2, 2013, provisional application No. 61/703,102, filed on Sep. 19, 2012.

(51) Int. Cl.
G01N 21/00 (2006.01)
G01N 21/01 (2006.01)
B05B 1/02 (2006.01)
G01N 15/14 (2006.01)

(52) U.S. Cl.
CPC ........ *G01N 21/00* (2013.01); *B05B 1/02* (2013.01); *G01N 15/1404* (2013.01); *G01N 21/01* (2013.01); *G01N 2015/149* (2013.01)

(58) Field of Classification Search
CPC .............. G01N 2021/6441; G01N 2021/6484; G01N 21/6402

USPC .............................. 356/72, 73, 343, 338, 399
See application file for complete search history.

(56) References Cited

U.S. PATENT DOCUMENTS 3,672,324 A 6/1972 Schnedler
3,893,766 A 7/1975 Hogg
(Continued)

FOREIGN PATENT DOCUMENTS

CA 2296324 A1 2/1999
CA 2739572 A1 11/2001
(Continued)

OTHER PUBLICATIONS

Australian Notice of Acceptance dated Jul. 24, 2014, issued in related AU Application No. 2013202615 (2 pp).
(Continued)

*Primary Examiner* — Kara E Geisel
*Assistant Examiner* — Iyabo S Alli
(74) *Attorney, Agent, or Firm* — Ryan Christensen; Hashim Rahman

(57) ABSTRACT

A nozzle tip formed from a cylindrical body defining a longitudinal axis and a frustoconical body adjoining the cylindrical body on the longitudinal axis. The cylindrical body may be in fluid communication with the frustoconical body. The frustoconical body may end in a flat surface with a nozzle exit orifice which is transverse to the longitudinal axis. There may be a cutout at the edge of the frustoconical body and the flat surface. The flow cytometer system may also include a source of electromagnetic radiation for producing a beam incident upon the fluid stream and the particles and a detector for detecting light emitted or reflected from the particles within the fluid stream in response to the beam.

23 Claims, 8 Drawing Sheets

(56) References Cited

U.S. PATENT DOCUMENTS

| | | | |
|---|---|---|---|
| 4,361,400 | A | 11/1982 | Gray et al. |
| 4,362,246 | A | 12/1982 | Adair |
| 4,660,971 | A | 4/1987 | Sage et al. |
| 4,737,025 | A | 4/1988 | Steen |
| 4,798,008 | A | 1/1989 | Belanger et al. |
| 4,813,609 | A | 3/1989 | French |
| 4,848,670 | A | 7/1989 | Belanger |
| 4,988,619 | A | 1/1991 | Pinkel |
| 5,088,816 | A | 2/1992 | Tomioka et al. |
| 5,135,759 | A | 8/1992 | Johnson |
| 5,311,290 | A | 5/1994 | Olson et al. |
| 5,371,585 | A | 12/1994 | Morgan et al. |
| 5,439,362 | A | 8/1995 | Spaulding |
| 5,466,572 | A | 11/1995 | Sasaki et al. |
| 5,483,469 | A | 1/1996 | Van den Engh et al. |
| 5,601,234 | A | 2/1997 | Larue |
| 5,602,039 | A | 2/1997 | Van den Engh |
| 5,602,349 | A | 2/1997 | Van den Engh |
| 5,660,997 | A | 8/1997 | Spaulding |
| 5,690,895 | A | 11/1997 | Matsumoto et al. |
| 5,700,692 | A | 12/1997 | Sweet |
| 5,726,364 | A | 3/1998 | Van den Engh |
| 5,985,216 | A | 11/1999 | Rens |
| 6,089,078 | A | 7/2000 | Chelveder |
| 6,133,044 | A | 10/2000 | Van den Engh |
| 6,149,867 | A | 11/2000 | Seidel |
| 6,263,745 | B1 | 7/2001 | Buchanan |
| 6,267,301 | B1 | 7/2001 | Haruch |
| 6,357,307 | B2 | 3/2002 | Buchanan |
| 6,372,506 | B1 | 4/2002 | Norton |
| 6,491,190 | B1 | 12/2002 | Dunworth |
| 6,604,435 | B2 | 8/2003 | Buchanan |
| 6,746,873 | B1 | 6/2004 | Buchanan |
| 6,782,768 | B2 | 8/2004 | Buchanan |
| 7,012,689 | B2 * | 3/2006 | Sharpe ............... G01N 15/14 356/399 |
| 7,024,316 | B1 | 4/2006 | Ellison et al. |
| 7,780,095 | B2 | 8/2010 | Babaev |
| 7,855,078 | B2 | 12/2010 | Evans |
| 7,923,252 | B2 | 4/2011 | Van den Engh |
| 8,043,553 | B1 | 10/2011 | Durcan |
| 9,027,850 | B2 | 5/2015 | Buchanan et al. |
| 2002/0084290 | A1 | 7/2002 | Materna |
| 2002/0175220 | A1 | 11/2002 | Pence |
| 2003/0042326 | A1 * | 3/2003 | Jameson ............... B01F 3/0815 239/102.2 |
| 2004/0053243 | A1 | 3/2004 | Evans et al. |
| 2005/0112541 | A1 | 5/2005 | Durack et al. |
| 2005/0180885 | A1 | 8/2005 | Tateishi |
| 2006/0141628 | A1 | 6/2006 | Evans |
| 2006/0263829 | A1 | 11/2006 | Evans et al. |
| 2007/0269348 | A1 | 11/2007 | Van Den Engh et al. |
| 2008/0113447 | A1 | 5/2008 | Krager et al. |
| 2008/0230632 | A1 | 9/2008 | Fenton et al. |
| 2011/0010144 | A1 | 1/2011 | Fox et al. |
| 2011/0076712 | A1 | 3/2011 | Gilligan |
| 2011/0259749 | A1 | 10/2011 | Kanda |
| 2012/0200857 | A1 | 8/2012 | Sharpe et al. |

FOREIGN PATENT DOCUMENTS

| | | |
|---|---|---|
| CN | 103013811 A | 4/2013 |
| EP | 0288029 | 4/1988 |
| EP | 1716798 A2 | 11/2006 |
| JP | H02 118852 | 9/1990 |
| JP | H05 034262 A | 2/1993 |
| WO | 96/12171 | 4/1996 |
| WO | 99/05504 | 7/1998 |
| WO | 01/40765 | 7/2001 |
| WO | 2004053243 A1 | 6/2004 |

OTHER PUBLICATIONS

US Office Action Issued on Nov. 18, 2014 for Related U.S. Appl. No. 13/831,254.

US Office Action Issued on Feb. 3, 2015 for Related U.S. Appl. No. 13/831,332.

Australian Examination Report issued Dec. 18, 2013, in related AU Application No. 2013202615 (4 pp.).

PCT International Search Report and Written Opinion dated Feb. 2, 2014, issued in related PCT Application No. PCT/US 2013/60730 (11 pp).

International Search Report dated Jul. 22, 2013 in related International Patent Application No. PCT/US2013/031787. (28 pages).

Dean, P.N., et al., "Hydrodynamic orientation of spermatozoa heads for flow cytometry", Biophys. J. 23: 7-13, 1978.

Fulwyler, M.J., "Hydrodynamic orientation of cells." J Histochem. Cytochem, 1977, 25:781-783.

Gurnsey, M.P., and Johnson, L.A., "Recent improvements in efficiency of flow cytometric sorting of X and Y-chromosome bearing sperm of domestic animals: a review", 1998, New Zealand Society of Animal Protection. 3 pages.

Johnson, L.A., et al., "Enhanced flow cytometic sorting of mammalian X and Y sperm: high speed sorting and orienting for artificial insemination", Theriogenology. 49 (1): 361. abstr., 1998.

Johnson, L.A., et al., "Flow cytometry of X- and Y-chromosome bearing sperm for DNA using an improved preparation method and staining with Hoechst 333-42", Gamete Research 17: 203-212, 1987.

Johnson L.A., et al., "Modification of a laser-based flow cytometer or high resolution DNA analysis of mammalian spermatozoa" Cytometry 7:266-273, 1986.

Johnson L.A., et al., "Improved flow sorting resolution of X- and Y-chromosome bearing viable sperm separation using dual staining and dead cell gating", Cytometry 17 (suppl 7): 83, 1994.

Johnson, L.A., et al., "Sex Preselection: High Speed Flow Cytometric Sorting of X and Y sperm for Maximum efficiency", Theriogenology 52: 1323-1341, 1999.

Johnson, L.A., et al., "Sex preselection in rabbits: Live births from X and Y sperm separated by DNA and cell sorting" Bio Reprod 41: 199-203, 1989.

Kachel, V., et al., "Uniform Lateral Orientation, Caused by Flow Forces, of Flat Particles in Flow-Through Systems", The Journal of Histochemistry and Cytochemistry, 1997, vol. 25, No. 7, pp. 774-780.

Rens, W., et al., "Improved Flow Cytometric Sorting of X- and Y-Chromosome Bearing Sperm: Substantial Increase in Yield of Sexed Semen", Molecular Reproduction and Development, 1999, pp. 50-56.

Rens, W., et al., "A Novel Nozzle for More Efficient Sperm Orientation to Improve Sorting Efficiency of X and Y Chromosome-Bearing Sperm", Technical Notes, Cytometry 33, 1998, pp. 476-481.

Siedel, G.E. Jr., et al., "Artificial insemination of heifers with cooled, unfrozen, and sexed semen." Theriogenoloy, 1998, 49 (1): 365.

Welch G.R., et al., "Fluidic and optical modifications to a ACS IV for flow sorting of X- and Y-chromosome bearing sperm based on DNA", Cytometry 17 (suppl. 7): 74, 1994.

US Notice of Allowance dated Mar. 2, 2015 issued in corresponding U.S. Appl. No. 13/831,254.

US Office Action dated Mar. 10, 2015 issued in corresponding U.S. Appl. No. 14/032,086.

AU Examination Report dated Apr. 13, 2015 issued in corresponding AU Application No. 2013202631.

New Zealand Office Action dated Apr. 22, 2015 in related NZ Patent Application No. 630373.

New Zealand Office Action dated Apr. 22, 2015 in related NZ Patent Application No. 706552.

New Zealand Office Action dated Jun. 15, 2015 in related NZ Patent Application No. 630368.

US Office Action dated May 21, 2015 in related U.S. Appl. No. 13/831,332.

US Office Action dated Oct. 9, 2015 issued in related U.S. Appl. No. 13/831,332.

CN Office Action dated Sep. 30, 2015 issued in related CN Application No. 201380048073.1.

* cited by examiner

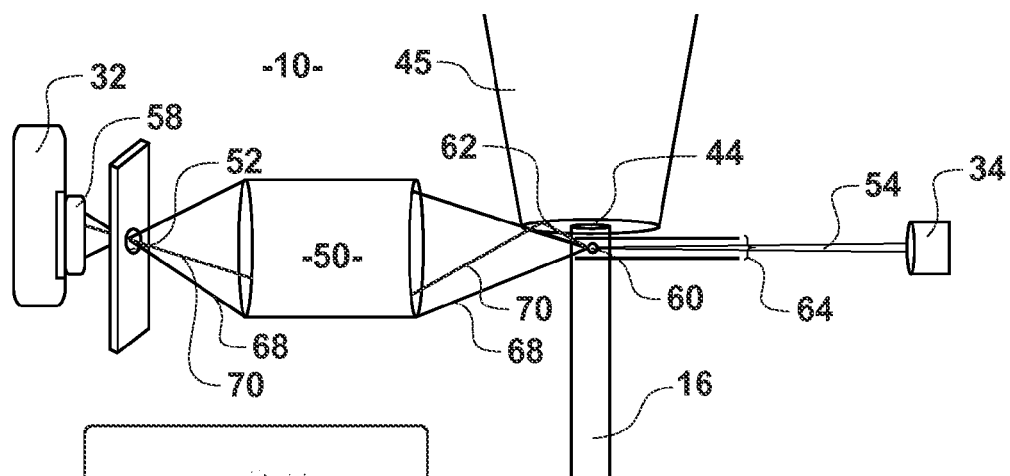
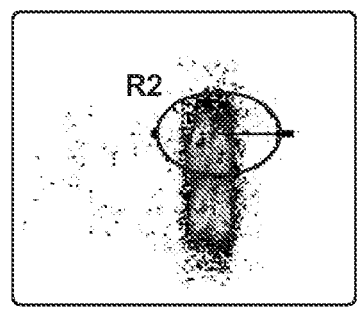
FIG. 7
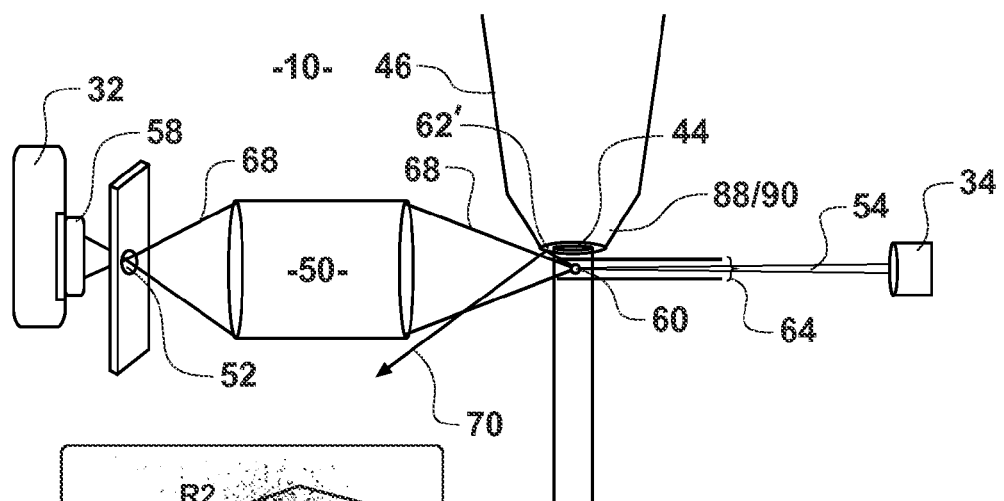
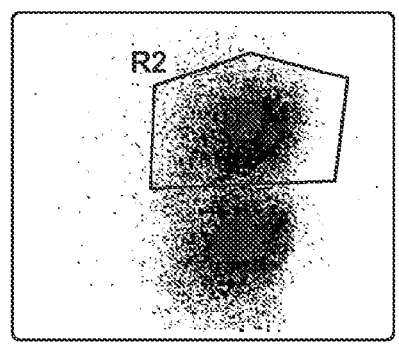
FIG. 9

FLOW CYTOMETER NOZZLE TIP

This non-provisional Patent Application claims the benefit of U.S. Provisional Patent Application No. 61/842,310, filed on Jul. 2, 2013, and U.S. Provisional Patent Application No. 61/703,102, filed Sep. 19, 2012, and International Patent Cooperation Treaty Patent Application PCT/US2013/031787, filed on Mar. 14, 2013, the entire contents of each of which are incorporated herein by reference.

FIELD OF THE INVENTION

The present invention generally relates to the field of flow cytometry and more particularly relates to improved nozzle tips for flow cytometer systems allowing detection closer to a nozzle exit orifice.

BACKGROUND

Flow cytometers are known for analyzing and sorting particles and are particularly suited to measure physical and chemical properties of biological materials, such as cells. During operation, a flow cytometer produces a fluid stream that entrains a sample fluid containing particles of interest. These particles may be individually inspected in the fluid stream by a variety of sensing systems or detection devices for classification.

Flow cytometers adapted for sorting additionally provide a mechanism for isolating subpopulations of particles based on their measured or determined properties. Jet-in-air flow cytometers achieve this separation through the creation and isolation of charged droplets containing particles of interest. The particle-containing droplets may be formed from the fluid stream and charged based upon a sort decision and, as they pass through an electrical field produced by deflection plates, their path is redirected into one of several predetermined trajectories for collection. The formation of these droplets may be achieved at a flow cytometer nozzle.

In addition to the function of droplet formation, some flow cytometer nozzles include an interior geometry that influences particles toward a uniform orientation. The orientating function enables analysis and sorting of cells with aspherical properties. As an example, the speeds at which sperm can be sorted into gender enriched populations have been increased, in part, due to the development of an orienting nozzle which presents a larger portion of the sperm to detectors in a relatively uniform orientation.

SUMMARY OF THE INVENTION

Certain embodiments of the claimed invention are summarized below. These embodiments are not intended to limit the scope of the claimed invention, but rather serve as brief descriptions of possible forms of the invention. The invention may encompass a variety of forms which differ from these summaries.

One embodiment relates to a flow cytometer system which has a nozzle assembly for producing a fluid stream with particles. The nozzle assembly may have a nozzle tip formed from a cylindrical body defining a longitudinal axis and a frustoconical body adjoining the cylindrical body on the longitudinal axis. The cylindrical body may be in fluid communication with the frustoconical body. The frustoconical body may end in a flat surface with a nozzle exit orifice which is transverse to the longitudinal axis. There may be a cutout at the edge of the frustoconical body and the flat surface. The flow cytometer system may also include a source of electromagnetic radiation for producing a beam incident upon the fluid stream and the particles and a detector for detecting light emitted or reflected from the particles within the fluid stream in response to the beam.

Another embodiment relates to a nozzle tip having a cylindrical body defining a longitudinal axis. A frustoconical body may adjoin, and be in fluid communication with, the cylindrical body on the longitudinal axis. The frustoconical body may end in a flat surface having a nozzle exit orifice transverse to the longitudinal axis. There may be a cutout at the edge of the frustoconical body and the flat surface.

BRIEF DESCRIPTION OF THE DRAWINGS

FIG. 6 illustrates a flow cytometer operating with an interrogation location near the ideal location, but with more occlusion light reflected from the nozzle into the pinhole.

FIG. 7 illustrates a bivariate plot obtained from flow cytometer sex sorting sperm in the configuration of FIG. 6.

FIG. 8 illustrates an embodiment of a flow cytometer system having a chamfered nozzle allowing the interrogation location to be located near to an ideal location without occlusion.

FIG. 9 illustrates a bivariate plot obtained from flow cytometer sex sorting sperm in the configuration of FIG. 8.

Figure 1:
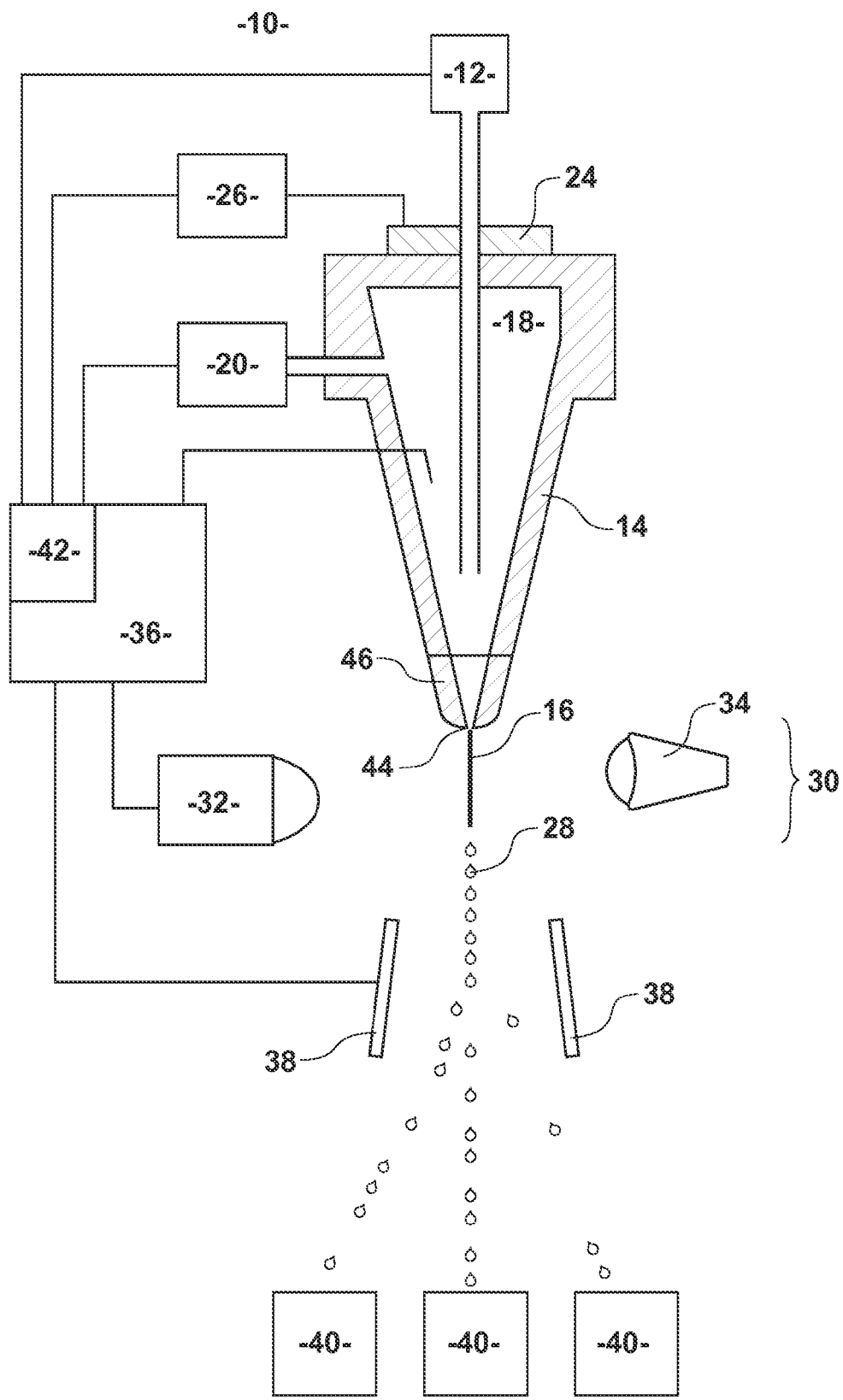
FIG. 1 illustrates a schematic of a flow cytometer.

While the present invention may be embodied with various modifications and alternative forms, specific embodiments are illustrated in the figures and described herein by way of illustrative examples. It should be understood the figures and detailed descriptions are not intended to limit the scope of the invention to the particular form disclosed, but that all modifications, alternatives, and equivalents falling within the spirit and scope of the claims are intended to be covered.

MODE(S) FOR CARRYING OUT THE INVENTION

In the field of flow cytometry, particles of interest generally include a large variety of cells. Each type of cell presents various constraints and limitations relating to the operating parameters of a flow cytometer instrument, particularly when the instrument is configured for sorting. For example, large cells require a larger nozzle exit orifice, while smaller cells often require a smaller nozzle exit orifice. Other smaller cells can be fragile and may require a larger nozzle exit orifice that decreases cell velocity and forms larger droplets. Other operational parameters, such as the sample pressure and the rate of droplet formation, may depend on the concentration of cells undergoing processing in combination with the size of the cells. In the case of sorting, desired sorting rates and purities may dictate additional limitations on operating parameters. In addition to the size of the cells, the shapes of the cells may dictate the interior geometry of the nozzle required for a jet-in-air flow cytometer system.

A standard nozzle tip may be configured to produce a coaxial laminar flow of two fluids through an unmodified tapered circular geometry. The resulting fluid stream comprises a cylindrical core stream surrounded by a coaxial outer stream. This fluid stream is well suited for round or semi-round cells. Such an unmodified nozzle tip injects cells into a cylindrical core shape with equal pressure applied to the core to center the cells within the core. The unmodified geometry provides equal pressure from all sides urging cells into a laminar single file flow. Because round, or semi round, cells present a high degree of symmetry they do not require orientation and can be analyzed properly regardless of their rotation in relation to either an interrogating laser or detectors. For this reason, the physical location along the fluid stream at which laser interrogation is performed in relation to the output of the nozzle tip is generally not a critical factor.

However, a certain subset of flow cytometer operations require modified nozzles that tend to present particles in a uniform orientation. Modified nozzles may produce a ribbon shaped core by providing a relatively high pressure in one plane and a relatively low pressure in a transverse plane. This geometry is particularly suited to bias flat or paddle shaped cells into a uniform orientation. Non-limiting examples of modified orienting nozzle geometries are described in U.S. Pat. Nos. 6,357,307, 6,604,435, 6,782,768, and 6,263,745, the entire contents of each of which are incorporated herein by reference. As one example, sperm sorting requires differentiating very small differences of a DNA selective dye. Due to the aspherical shape of sperm cells, these differences can only be accurately determined in cells that are uniformly oriented facing the excitation source for full illumination and of emissions from the cells with respect to a detector.

In addition to various factors described above, several aspects of the flow cytometer must be calibrated to differentiate X-chromosome bearing sperm from Y-chromosome bearing sperm. One feature that must be determined is the vertical placement of the interrogation location, or the beam spot, on the fluid stream. An ideal location on the fluid stream generally coincides with the location at which the greatest percentage of sperm presents the desired orientation and the narrowest section of the core stream. Such an ideal location may be determined empirically while sperm are analyzed in a calibration run prior to sorting.

In many nozzles, interrogation locations closer to the nozzle exit orifice demonstrate increasingly better performance. Whether because sperm are living cells which tend to become un-oriented, or because sperm become over-oriented as they continue down the fluid stream, it appears measurements are often more precise as the interrogation location approaches the nozzle tip. However, as the interrogation location approaches current orienting nozzle tips, artifacts are introduced which decrease the performance of the system. In particular, light emissions reflected off the bottom surface of current tips causes artifacts in the detection signal. In most cases, these types of artifacts decrease system performance resulting in a distorted image and overall decreases in the intensities of signals detected. In the absence of such artifacts, the vertical placement of the interrogation zone closer to a nozzle tip may be possible and resulting in better resolution, as well as, faster sorting speeds with minimal losses in signal quality.

In contrast to orienting nozzles, typical round or semi-round cells may be aligned within standard nozzles in a larger range of vertical positions without decreasing the signal quality. Stated differently, round cells can be interrogated with equal effectiveness over a relatively large vertical range in the fluid stream as compared to cells requiring orientation.

Referring to FIG. 1, a flow cytometer system (10) is illustrated which may incorporate a modified nozzle tip (46) in accordance with embodiments described herein. While the flow cytometer system (10) is depicted as a jet-in-air flow cytometer with sorting components, it should be understood the nozzle tips described herein may be incorporated in other analytical instruments which may not perform sorting functions. The flow cytometer system (10) includes a cell source (12) for producing a fluid stream containing particles of interest. The flow of sample is deposited within a nozzle assembly (14) and introduced into, or flowed into, a fluid stream (16) of sheath fluid (18). The sheath fluid (18) can be supplied by a sheath fluid source (20) so that as the cell source (12) supplies the particles into the sheath fluid (18) they are concurrently fed through the nozzle assembly (14). The sheath fluid (18) may be supplied at a sheath flow rate which is determined by a sheath pressure applied at the sheath fluid source (20). In this manner, the sheath fluid (18) forms a fluid stream (16) coaxially surrounding the sample having particles which exit the nozzle assembly (14) through the nozzle tip (46) at the nozzle exit orifice (44). An oscillator (24) may be precisely controlled with an oscillator control (26), to produce pressure waves within the nozzle assembly (14) and the pressure waves may be transmitted to the fluids exiting the nozzle assembly (14) at nozzle exit orifice (44). In response to the pressure waves, the fluid stream (16) exiting the nozzle exit orifice (44) eventually forms regular droplets (28) at precise intervals. The frequency, and to some extent the shape of the formed droplets may be controlled by a drop drive frequency and drop drive amplitude supplied to the oscillator (24) or the oscillator controller (26).

Each droplet, so formed, retains the sheath fluid and sample that previously formed a portion of the fluid stream (16). Because the cells supplied from the cell source (20) are surrounded by the fluid stream (16) or sheath fluid environment, the droplets (28) ideally contain individually isolated cells. However, the sample concentration, sample pressure, and other instrument parameters dictate the frequency with which multiple cells will regularly occupy a single droplet, as well as the percentage of droplets containing sperm cells.

The flow cytometer (10) acts to sort droplets based on the characteristics of cells predicted to be contained within the droplets. This can be accomplished through a cell sensing system (30) in communication with an analyzer (36). The cell sensing system (30) includes at least one sensor, or detector, (32) responsive to the cells contained within fluid stream (16). The cell sensing system (30) provides data to the analyzer (36), which may cause an action depending upon the relative presence or relative absence of a characteristic of cells in the fluid stream (16). Certain characteristics, such as the relative DNA content of sperm cells, can be detected through excitation with a source of electromagnetic radiation (34), such as a laser generating an irradiation beam to which the cells are responsive. As a non-limiting example, the cells may be sperm cells stained with Hoechst 33342, and the source of electromagnetic radiation (34) may be a laser operated at UV wavelength, such as at about 355 nm. An example of such a laser can be a Vanguard 350 (available from Spectra-Physics), which operates at 350 mW. Various optics may be employed to shape the beam profile of the laser, split the beam to more than one stream, or reduce the beam power at a stream. Non-limiting examples of such optics can be found in WO/2004/104178 and WO/2001/85913, each being incorporated herein by reference.

In the case of sperm, the presence of an X-chromosome or a Y-chromosome can be determined from the detected fluorescence produced in response to the electromagnetic radiation source (34). In particular, configurations of the cell sensing system (30) may be in communication with an analyzer for providing a variety of fluorescence information, such as the forward fluorescence of an event, the side fluorescence of an event, or the amount of scatter associated with an event. The analyzer (36) may include written instructions for analyzing the signals produced by the one or more sensors (32) in the cell sensing system (30). The DNA selective fluorescent dye binds stoichiometrically to sperm DNA. Because X-chromosome bearing sperm contain more DNA than Y-chromosome bearing sperm, the X-chromosome bearing sperm can bind a greater amount of DNA selective fluorescent dye than Y-chromosome bearing sperm. Thus, by measuring the fluorescence emitted by the bound dye upon excitation, it is possible to differentiate between X-bearing spermatozoa and Y-bearing spermatozoa. Distinctions, such as sperm which is viable or not viable, may be differentiated in addition to oriented and unoriented sperm by the analyzer (36) according to sorting logic incorporated with gating regions.

In order to achieve separation and isolation based upon stained sperm characteristics, emitted light can be detected by the sensor (32) and the information fed to an analyzer (36) coupled to a droplet charger which differentially charges each droplet (28) based upon the characteristics of the stained sperm contained within that droplet (28). In this manner the analyzer (36) acts to permit the electrostatic deflection plates (38) to deflect droplets (28) based on whether or not they contain the appropriate particle or cell.

As a result, the flow cytometer (10) acts to separate stained sperm by causing the droplets (28) containing sperm to be directed to one or more collection containers (40). For example, when the analyzer differentiates sperm cells based upon a sperm cell characteristic, the droplets entraining X-chromosome bearing spermatozoa can be charged positively and thus deflect in one direction, while the droplets entraining Y-chromosome bearing spermatozoa can be charged negatively and thus deflect the other way, and the wasted stream (that is droplets that do not entrain a particle or cell or entrain undesired or unsortable cells) can be left uncharged and thus collected in an undeflected stream into a suction tube or the like. Alternatively, one of the X-chromosome bearing sperm or the Y-chromosome bearing sperm may be collected, while the other is discarded with waste.

A controller (42) may form a portion of the analyzer (36) or may be a component external to the analyzer (36). The illustrated controller (42) may also represent a collection of individual controllers. The controller (42) may receive signals or instructions from the analyzer (36) and in response may modify one or more instrument parameters, such as the sample flow rate, sample pressure, sheath flow rate, sheath pressure, drop drive frequency, or drop drive amplitude and the like. The controller (42) may also provide an interface for operator input to manually adjust the sample flow rate, sample pressure, sheath flow rate, sheath pressure, drop drive frequency, drop drive amplitude and the like. The analyzer (36) may include written instructions for modifying the instrument parameters in response to measured sorting parameters, or modifications to instrument parameters may be manually performed by an operator adjusting various settings. The modifications to instrument parameters may be carried out in the analyzer (36) such as for changing sorting logic, abort logic, sorting regions, or gate regions and other parameters specific to making sort decisions in the analyzer. Additional modifications to instrument parameters may be effected by a controller (42), which may control various external components to the analyzer, such as controlling the sample pressure, sample flow rate, sheath pressure, sheath flow rate, drop drive frequency, and drop drive amplitude.

Figure 2:
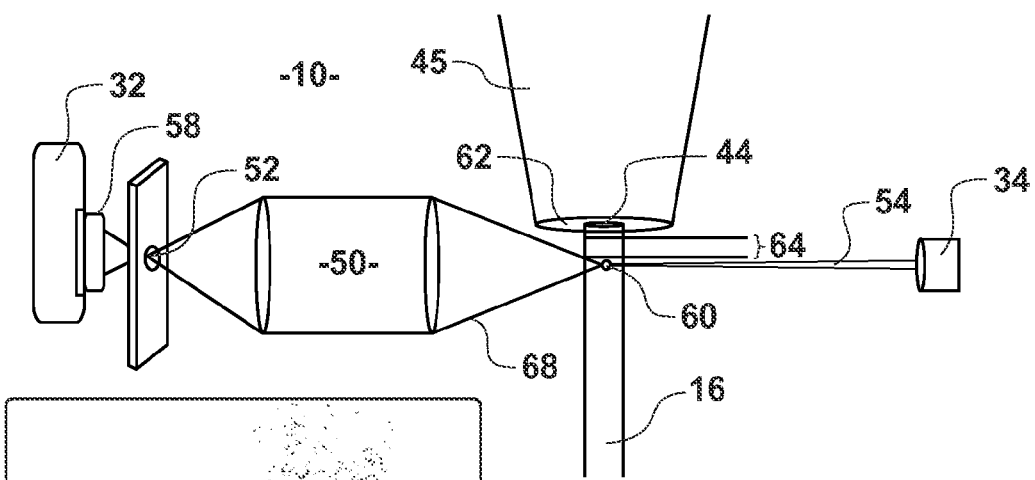
FIG. 2 illustrates a flow cytometer operating outside an ideal vertical position on a fluid stream.

FIG. 2 illustrates a portion of a flow cytometer system (10) including a unmodified orienting nozzle tip (45) having a nozzle exit orifice (44) in a flat bottom surface (62). A source of electromagnetic radiation (34) is illustrated producing a laser beam (54) in the 355 nm wavelength range which is focused at an interrogation location (60) on the fluid stream (16) some distance below the nozzle tip (45). The interrogation location (60) can be seen at a vertical location below an indicated ideal range of locations (64). Emissions (68), or electromagnetic radiation which is emitted from or reflected from cells interrogated at the interrogation location (60), are illustrated as diverging rays that are collected at an objective lens (50) and focused through a pinhole (52) in a pinhole strip to an optical filter (58) and a sensor, which can be a detector (32), such as a photomultiplier tube (PMT). Arrangements of detectors may also be employed in known manners. For example, in the field of sperm sorting, orthogonal fluorescence detectors may be placed in the forward and side locations.

Figure 3:
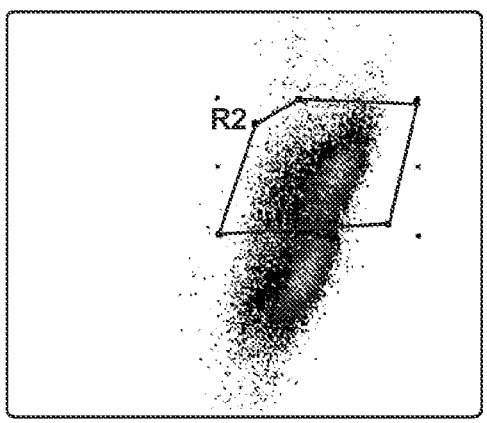
FIG. 3 illustrates a bivariate plot obtained from flow cytometer sex sorting sperm in the configuration of FIG. 2.

FIG. 3 illustrates a bivariate plot representing information produced from the flow cytometer system (10) partially illustrated in FIG. 2. The bivariate plot may be generated by manipulating signals produced by one or more detectors which detect fluorescence emissions from cells in the fluid stream. The illustrated bivariate plot is generated during the sex sorting process of sperm and represents a peak height on one axis and an integrated area on the other axis detected from a population of stained sperm. Within the bivariate plot, two emerging sub-populations can be seen. While some overlap does exist, these populations may be gated and sorted into one or more populations. In the sperm sorting operation, R2 represents a gating region which includes sperm to be sorted as live X-chromosome bearing sperm. However, resolution and signal intensity seen in FIG. 3 may be suboptimal and may require the flow cytometer system to be run at lower speeds in order to achieve a desired purity and/or a desired yield.

Figure 4:
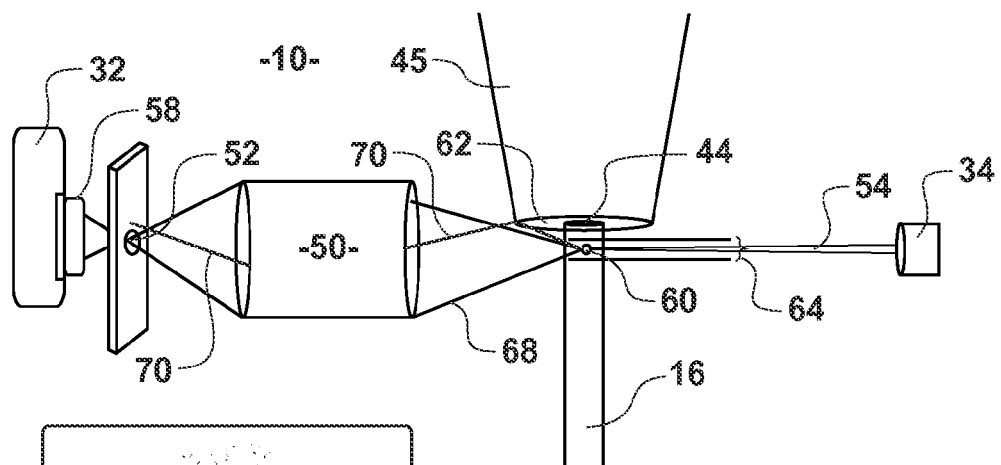
FIG. 4 illustrates a flow cytometer operating with an interrogation location closer to an ideal location, but with some occlusion of the resulting emissions.
Figure 5:
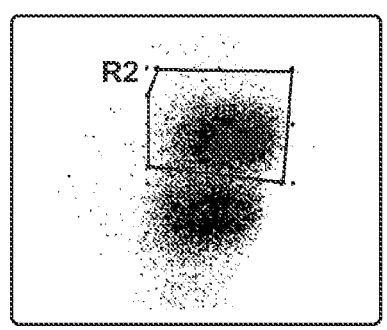
FIG. 5 illustrates a bivariate plot obtained from flow cytometer sex sorting sperm in the configuration of FIG. 4.

FIG. 4 illustrates the flow cytometer system (10) as FIG. 2, except that the laser beam (54) has been moved within the ideal range of locations (64) (which may also be referred to as the ideal range of vertical positions). For illustrative purposes this ideal range of locations (64) coincides with the location at which occlusion of some of the emissions (68) begin. In addition to the emissions (68), a representative secondary emission (70) is illustrated being reflected off the flat surface (62) of the unmodified nozzle tip (45) and through the objective lens (50). FIG. 5 illustrates a representative bivariate plot of signals produced by the configuration illustrated in FIG. 4. While not readily apparent from the bivariate plot, the overall peak intensities may be lower for both populations of sperm due to occlusion. Additionally, because of the divergent nature of fluorescent light, some fraction of reflected light may be entering the pin hole resulting in noise and/or distortion.

Turing now to FIG. 6, as the interrogation location (60) is moved even closer to the unmodified nozzle tip (45). The additional reduction in this distance between the interrogation location (60) and the nozzle tip (45) results in an increases both the occlusion of the emissions (68) and the amount of secondary emissions (70) being reflected off the flat bottom (62) of the nozzle tip (45). In the field of sperm sorting it has been observed that at some distance the geometry of the objective lens and the nozzle tip can actually place the secondary emissions directly into the pin hole (52) at a slightly different timing causing distortion. FIG. 7 illustrates a bivariate lot, like FIG. 5, but with a high degree of distortion. Each of the typical X and Y chromosome bearing sperm populations themselves resemble two populations, leaving an appearance of four populations. Two additional populations may result in certain flow cytometer instruments from these secondary emissions which reach the detector after a slight delay.

FIG. 8 illustrates a configuration with a modified nozzle tip (46) having a reduced area flat surface (62') and a cutout (88) in the form of a chamfer (90). These features addresses a previously unrecognized problem by eliminating a portion of the flat surface responsible for occluding emissions (68) and reflecting secondary emissions (70). The modified nozzle tip (46) may be characterized as chamfered (90), but other methods of trimming portions of the flat surface (62) are also contemplated. FIG. 8 illustrates the interrogation location (60) being placed on or near the ideal location and in the same location as illustrated in FIG. 6, with minimal secondary emissions (70) reflected due to the geometry of the bottom surface (62'). Secondary emissions (70) which are reflected will no longer have the former geometric pathway available to the pinhole (52). Instead, a greater portion of the emitted light (68) from the interrogation location (60) is directly captured by the objective lens (50).

As seen in FIG. 9, the resulting bivariate plot illustrates two distinct populations of sperm. As such, the modified nozzle tip allows the normal operation of the flow cytometer over an increased range of positions for the beam spot, including a range closer to the nozzle tip which provides improved performance.

As used herein the term "frustoconical" may be understood as describing the general shape of a truncated cone, but is intended to include minor variations from the strict mathematical definition and may include chamfers, fillets, or other curvatures or rounded portions, particularly at, or near, any edges.

The term "frustoconical body" may be understood as describing a body having the general shape of a truncated cone, but is intended to include minor variations from the strict mathematical definition of such a shape and may include variations such as chamfers, fillets, or other curvatures or rounded portions, particularly at, or near, any edges.

The term "cylindrical body" may be understood as describing a body having the general shape of a cylinder, but is intended to include minor variations from the strict mathematical definition of such a shape and may include variations including notches, grooves, flanges, rounded edges, chamfer and other alterations.

As used herein the term "cutout" should be understood as referring the surface of an object having the appearance that adjoining material was cut, or shaved, or otherwise removed at that surface. However, that surface may be formed by any number of techniques and no physical removal of material in necessary. For example, a piece may be formed from injection molding or with a 3-D printer any may have a surface giving the appearance of a chamfer, fillet or other groove and this surface may be considered a "cutout" as used herein.

Figure 10:
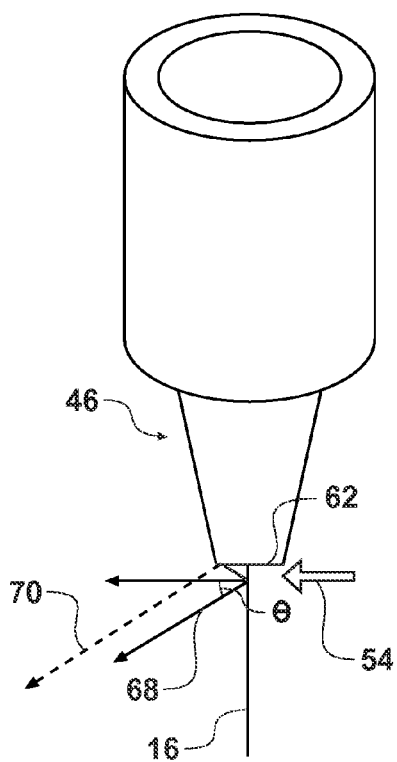
FIG. 10 illustrates a portion of a flow cytometer operating with an interrogation location at a particular distance from a nozzle tip.
Figure 11:
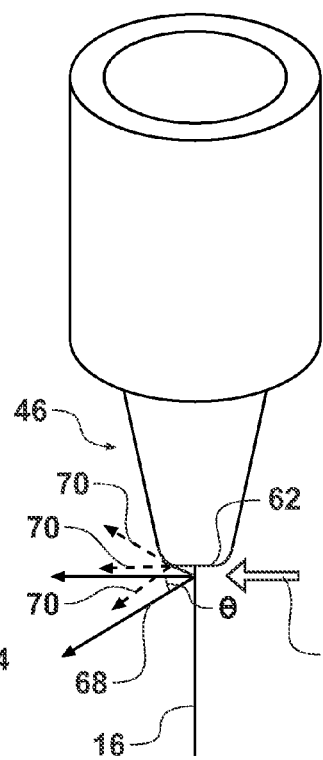
FIG. 11 illustrates a portion of a flow cytometer operating with an interrogation location at a particular distance from a nozzle tip.
Figure 12:
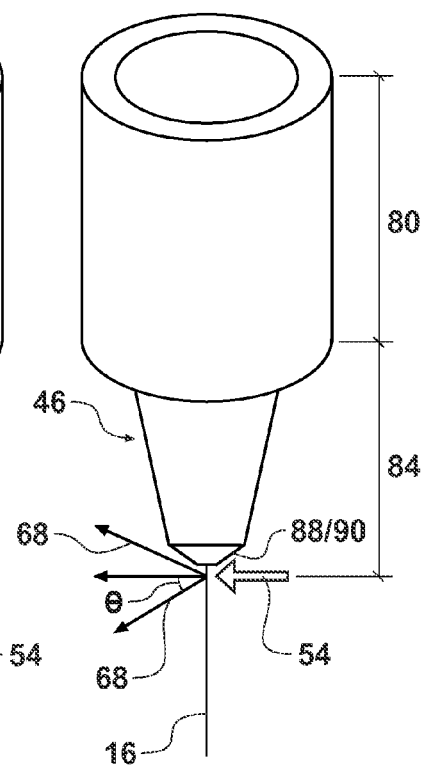
FIG. 12 illustrates a portion of a flow cytometer operating with an interrogation location at a particular distance from the chamfered nozzle tip.

Turning now to FIGS. 10-12 a laser beam (54) is illustrated interacting with three different nozzle tips at the same distance. FIG. 10 illustrates an unmodified nozzle tip (45) having a flat bottom surface. FIG. 11 illustrates another unmodified nozzle tip (45) having a flat bottom surface, but which has a rounded transition to the flat bottom surface. Each nozzle tip produces a fluid stream that is inspected at an interrogation zone at the same location. Emission (68) results from a cell, or a stained cell, being interrogated with electromagnetic radiation at the interrogation zone. The emissions (68) are illustrated as a representative emissions cone having an angle of θ. The angle of the emission cone may be about 30 degrees in every direction.

In FIG. 10 the unmodified nozzle tip (45) is illustrated having a relatively large flat surface (62). At the illustrated distance, emissions (68) from particles in the fluid stream (16) are reflected off the flat surface (62) of the nozzle tip (45). Similarly, in FIG. 11, an unmodified nozzle tip (45) has more curved features, but still has a relatively large flat surface (62) that reflects secondary emissions (70) from particles in the fluid stream (16). The terminus of existing rounded nozzle tips having internal geometries for orienting cells is still a flat surface. Even in these rounded tips, the flat bottom surface occupies sufficient area to distort measurements taken in a close proximity to the unmodified nozzle tip (45).

In accordance with certain improved embodiments of nozzle tips, FIG. 12 illustrates a modified nozzle tip (46) having a cylindrical body (80) defining a longitudinal axis. A frustoconical body (84) is adjacent to the cylindrical body (80) along the longitudinal axis and in fluid communication with the cylindrical body. A cutout (88) at the tip of the frustoconical body (84) is in the form of a chamfer (90) leaving a flat surface with a minimal area. The flat surface (62) may have a reduced area as compared to prior nozzles, particularly prior nozzle with orienting geometries. This modified geometry accommodates the entire cone of emissions (68) without occlusion and without producing a secondary emission (70), allowing measurements to be taken closer to the modified nozzle tip (46) than the unmodified nozzle tips (45) of FIGS. 10 and 11.

Figure 13:
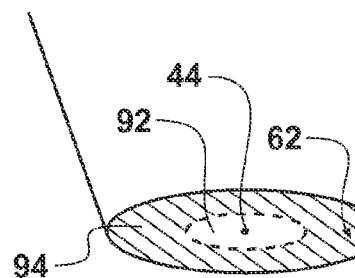
FIG. 13 illustrates an enlarged view of the end of the nozzle tip illustrated in FIG. 10.

FIG. 13 illustrates an extremely close view of the flat surface (62) on the bottom of the unmodified nozzle tip (45) seen in FIG. 10. An outer region (94) represents the area on the flat surface responsible for occluding emissions and reflecting secondary emissions at a particular distance from the nozzle. Whereas, the center region (92), represents the area on the bottom surface which does not occlude emissions or reflect secondary emissions at a particular distance from the nozzle. In some embodiments of a modified nozzle tip (46), the modified nozzle tip (46) may be provided with a reduced area flat surface (62') having the same surface area as the center region (92) illustrated.

Figure 14:
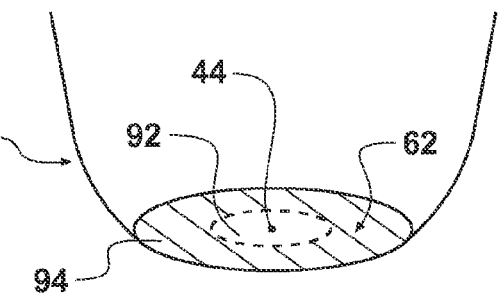
FIG. 14 illustrates an enlarged view of the end of the nozzle tip illustrated in FIG. 11.

Similarly, FIG. 14 illustrates the very bottom of an unmodified rounded nozzle tip (45), like that seen in FIG. 11. The corresponding outer region (94), includes less area than in FIG. 13, but a significant portion of the flat surface (62) is still problematic when attempting to interrogate a fluid stream at a position close to the nozzle tip.

Figure 15:
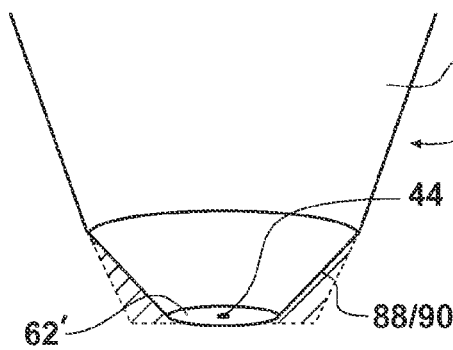
FIG. 15 illustrates an enlarged view of the end of the nozzle tip illustrated in FIG. 12.

FIG. 15 illustrates the very end of a modified nozzle tip (46), like that seen in FIG. 12, which may be characterized as the distal end of a frustoconical body (84). The frustoconical body (84) may be considered a single frustoconical body (84) having a chamfered tip (90), or may be considered a first frustocoical body having a first angle of taper adjacent to and continuous with a second frustoconical body having a second angle of taper. The second angle may be a more aggressive taper to reduce the size of the flat bottom surface having the nozzle exit orifice (44).

Figure 16:
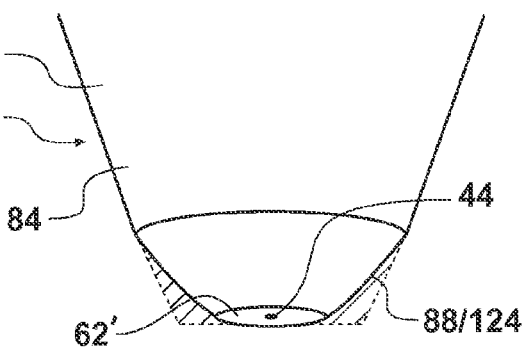
FIG. 16 illustrates an enlarged view of another embodiment of a nozzle tip.

FIG. 16 illustrates an alternative embodiment of a modified nozzle tip (46) where a cutout (88) resembles a rounded tip which ends in flat bottom surface with a reduced area (62'). This illustrated cutout (88) may also be characterized as a convex fillet (124) which terminates in a bottom surface having a reduced area (62').

Figure 17:
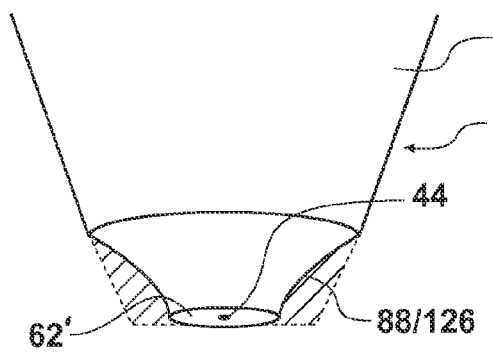
FIG. 17 illustrates an enlarged view of another embodiment of a nozzle tip.

FIG. 17 illustrates an alternative embodiment of a modified nozzle tip (46) where a cutout (88) is in the form of a concave fillet (126). The concave fillet (126) terminates in a reduced area (62') providing similar benefits conferred by the modified geometries illustrated in FIGS. 12 and 15.

Figure 18:
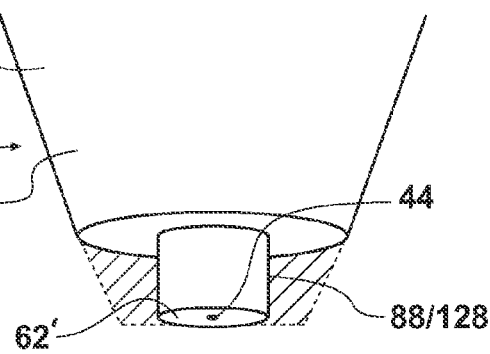
FIG. 18 illustrates an enlarged view of another embodiment of a nozzle tip.

FIG. 18 illustrates an alternative embodiment where the cutout is in the form of a perpendicular groove (128) resulting in the appearance of a second cylindrical body in communication with the frustoconical body (84). Alternatively, the second cylindrical body may have a wider base than the reduced area (62') flat bottom surface, which may be characterized as a second frustconical body, but not a chamfer like FIG. 15.

Figure 19:
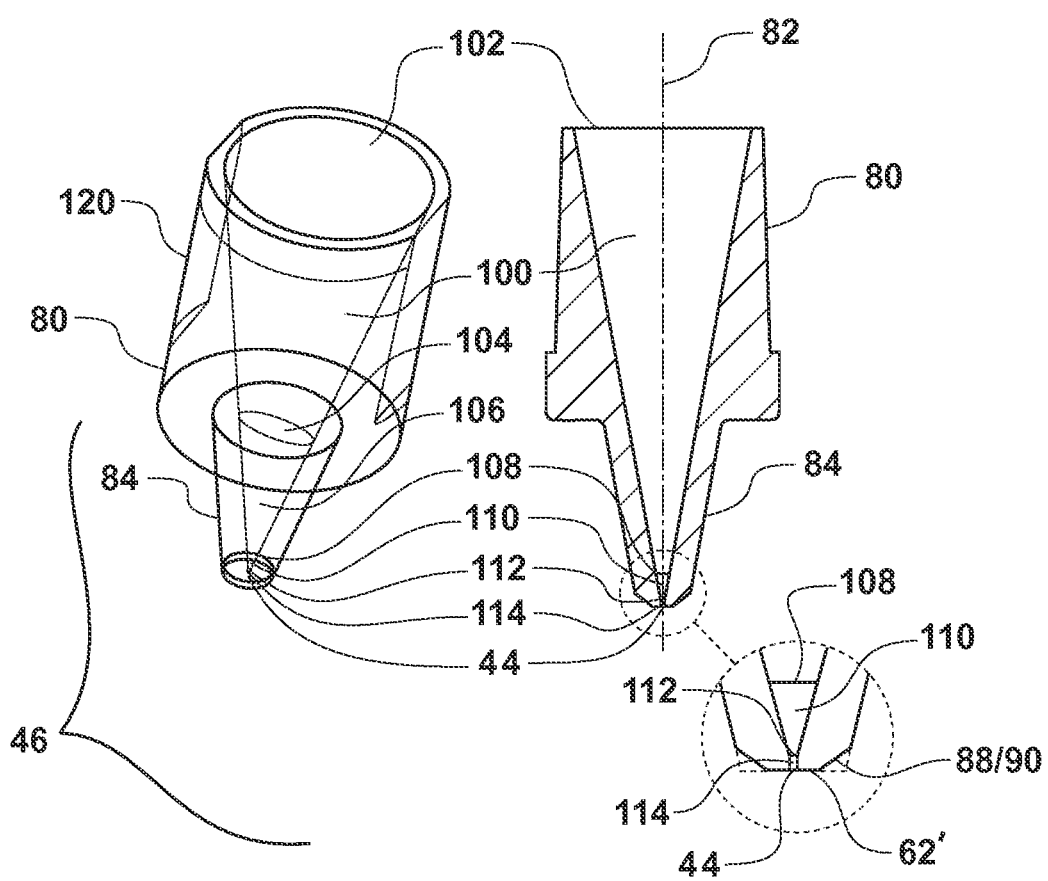
FIG. 19 illustrates an embodiment of a nozzle tip.

FIG. 19 illustrates a perspective view and a sectional view of a modified nozzle tip (46) having a cutaway (88) in the form of a chamfer (90) and an interior surface configured for orienting particles. The illustrated cutaway (88) is in the form of a chamfer (90), but other cutaways, like those illustrated in FIGS. 16-18 are expected to provide similar benefits. The exterior surface of the nozzle tip (46) may be characterized as a cylindrical body (80) adjacent to, and in fluid communication with, a frustoconical body (84) along a longitudinal axis (82). Additionally, there may be notches (120) or grooves formed in the exterior surface of the cylindrical body (80) for the purpose of securing the nozzle tip (46) with a nozzle assembly and/or for aligning the orienting nozzle tip (46) within a nozzle assembly. The bottom portion of the illustrated exterior surface may be characterized as a frustoconical body (84) ending in a chamfer (90), or may be characterized as a proximal portion of the frustoconical body which has a first angle of taper adjacent to a distal portion of the frustoconical body which has a second angle of taper; the second angle of taper being steeper than the first angle of taper.

Referring to the interior of the orienting nozzle tip (46) a generally circular mouth (102) to a nozzle tip cavity is formed along the longitudinal axis (82). The interior surface of the nozzle tip (46) may transition from a circular, or nearly circular, profile to an increasingly elliptical profile along an elliptically increasing region (100). The ratio of the major axis to the minor axis may increase until an elliptical demarcation (104), after which the elliptical profile of the interior surface may transition back towards a circular profile along the longitudinal axis (82) in an elliptically decreasing region (106). The elliptically decreasing region (106) may end at a circular demarcation (108) followed along the longitudinal axis (82) by a conical region (110). The conical region (110) may end at a second circular demarcation (112) which begins a cylindrical region (114) ending in the nozzle exit orifice (44).

A closer view of the terminus of the nozzle tip (46) illustrates the interior conical region (110) in addition to the cylindrical region (114) on the interior of the nozzle tip (46), as well as, the cutout (88) in the form of a chamfer (90). The nozzle exit orifice (44) may also be seen in this view formed in the flat bottom surface (62') which is transverse to the longitudinal axis (82).

One embodiment relates to the incorporation of the chamfered nozzle tip into an alternative nozzle assembly. One example of an alternative nozzle assembly may include a straight injection tube which is seated with a portion of the nozzle assembly. By reducing the overall length of the injection tube, it becomes easier to control the length and radial position of the injection outlet. Previous injection tubes often included metallic injection tubes which were bent within the nozzle assembly or which were straightened from coiled, or curved, stock. Whether introduced in a pre-fabrication coiling step or just prior to deployment in a flow cytometer nozzle, such curvatures result in folds or irregularities on the interior of the injection tube and may further create positional uncertainty of the injection tube central axis with respect to the desired flow axis within a nozzle. These folds and irregularities can inhibit laminar fluid flow or can redirect sample flow, which may have a negative impact on the performance characteristics of the nozzle assembly; particularly if orienting characteristics are desired. In another aspect, the over molded injection tube described herein may present a continuous, or flush, surface at any connection point.

Various previous nozzle assemblies often included connectors which presented dead volumes in the flow path. These dead volumes can become stagnant pockets of fluid that may harbor bacteria detrimental to the sample and may be difficult to clean. By injection over molding an injection tube into the nozzle assembly a precise, repeatable length and position can be achieved, thereby providing a reliable means of manufacturing nozzle assemblies with precise, reproducible performance characteristics. Additionally, over molding may provide a means for reducing or eliminating dead spaces at various connections. Additional elements may be over molded, or injection molded, with various portions of the nozzle assembly to reduce the number of potential dead spaces as well as the number of connections with the potential for leaking.

Figure 20:
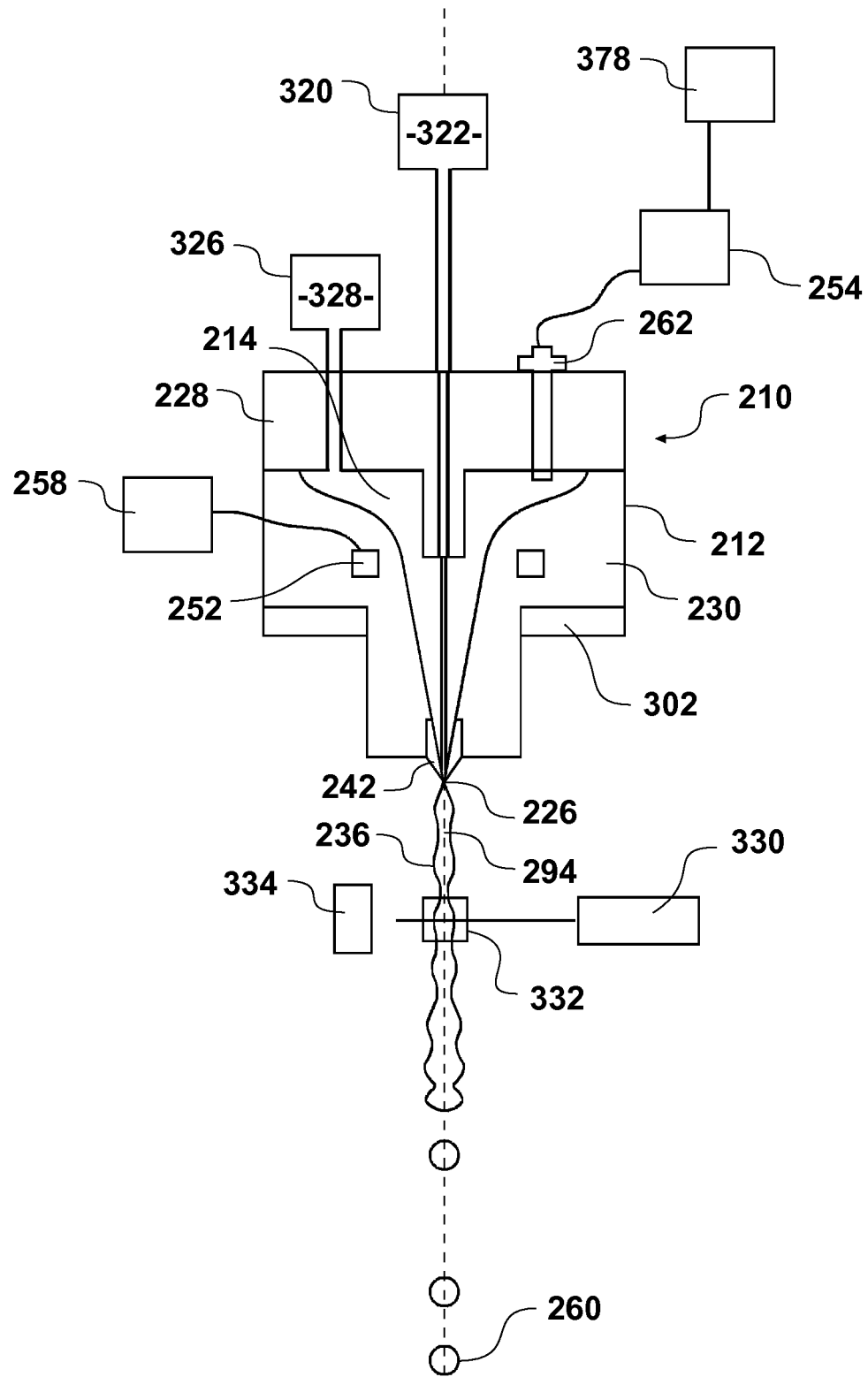
FIG. 20 illustrates an embodiment of a nozzle assembly.

Turning now to FIG. 20, a flow cytometer system is illustrated which incorporates one example of a nozzle assembly (210). The nozzle assembly (210) may be incorporated at the sort head of any number of commercially available droplet sorters, such as jet-in-air flow cytometers. The nozzle assembly (210) may include a nozzle housing (212) which encloses a nozzle cavity (214). The nozzle housing (212) may be constructed from a single molded housing piece, or may be assembled from a collection of nozzle housing pieces (244), such as two, three, four or more nozzle housing pieces. FIG. 20 illustrates a nozzle assembly (210) which includes two nozzle housing pieces (244a), (244b) in the form of a nozzle cap (228) secured to a nozzle base (230).

The flow cytometer system may include a sheath source (326) fluidically coupled to the nozzle assembly (210) for proving sheath fluid (328) to the nozzle assembly (210). A sample source (320) may also be coupled to the nozzle assembly (210) for providing sample fluid (322) to the nozzle assembly (210). The sample fluid (322) and sheath fluid (328) may be introduced into a nozzle cavity (214) under pressure and then passed through a nozzle tip (242) having a nozzle exit orifice (226) to form a fluid steam (236) along a flow path having a flow axis (294). The interior of the nozzle assembly (210) may be configured for producing a fluid stream (236) from the nozzle exit orifice (226) in the form of coaxial stream having an inner core stream of sample fluid (322) surrounded by an outer stream of sheath fluid (328).

An oscillating element (252), such as a piezoelectric crystal, may be located within the nozzle assembly (210) for perturbing the fluid stream (236) into droplets (260) some distance below the nozzle exit orifice (226). Previous oscillating elements have been located either above the nozzle cavity or within the nozzle cavity at the top of the cavity. One aspect of the current nozzle assembly (210) relates to an oscillating element (252) which is positioned to surround a portion of the nozzle cavity (214) and reduces the distance between the oscillating element (252) and the nozzle exit orifice (226). The oscillating element (252) may have a ring or toroidal shape with an outer diameter and an inner diameter and may be in communication with a controller (258). The controller (258) may produce a drive signal, such as between about 10 kHz and 120 kHz for perturbing the fluid stream (236) into between about 20,000 droplets per second and 120,000 droplets per second. Frequency and amplitude of the drive signal may be manipulated and/or adjusted by a user through a graphic user interface or through hardware. As but one example, the oscillating element (252) may be located about mid way down the nozzle assembly (210) surrounding the nozzle cavity (214). This location may be within the nozzle housing (212), or external to the nozzle housing (212), but mechanically coupled to the housing. Irrespective of the internal or external location, such an axial placement of the oscillating element (252) is believed to produce droplets more efficiently. In this configuration mechanical vibrations are transferred through nozzle assembly (210) and through the sheath fluid (328) in a speaker like manner to produce a pulsing characteristic in the fluid stream (236). This pulsing characteristic eventually breaks the fluid stream (236) into droplets (260) some distance below the nozzle exit orifice (226). Independent of other inventive features described herein, this application contemplates the benefit of modifying the placement of an oscillating element (252) within or coupled to any nozzle for increased efficiency in producing droplets.

A charge pin (262) may be mounted with the nozzle assembly (210). The charge pin (262) may be constructed from any electrically conductive material and provides an electrical connection between a charging element (252) and sheath fluid (328) contained in the nozzle cavity (214). Through the charge pin (262) a charge may be imparted to the entire fluid stream (236), including a forming droplet just prior to breaking away from the fluid stream (236). An analyzer (378) or other processing device may determine physical or chemical characteristics of particles in the sample and may classify the particles into one or more subpopulations. Based on any instructions relating to the subpopulation in which a particle is classified and other sorting parameters, including a calibrated drop delay, the analyzer (378) will instruct a charge circuit (254) to charge the fluid stream (236) by charging the charge pin (262) just prior to the formation of a droplet in which that particle is expected. In this way, droplets (260) may be supplied with a specific charge, including no charge, based on the characteristics of particles contained within them.

The nozzle assembly (210) may include a nozzle seat (302) for coupling into position on the flow cytometer system. Whereas previous nozzles may have been secured to adjustable stages with fasteners (such as screws, bolts etc.), the nozzle assembly (210) may include a nozzle seat (302) constructed free from fasteners. As one example, the nozzle seat (302) may be coupled to a flow cytometer without the aid of fasteners.

An excitation source (330), such as a source of electromagnetic radiation may be directed to a region know as an inspection zone (332) on the fluid stream (236). Particles within the fluid stream may reflect and/or emit electromagnetic radiation in response to this excitation, and this reflected and emitted electromagnetic radiation may be sensed by one or more detectors (334). These detectors (334) may produce signals representative of the emitted or reflected electromagnetic radiation (336), and those signals may be processed by an analyzer or a detection system to derive a number of chemical and physical properties. The analyzer (378) may then provide instructions to the charge circuit (254) in order to effect the appropriate sort action.

Figure 21:
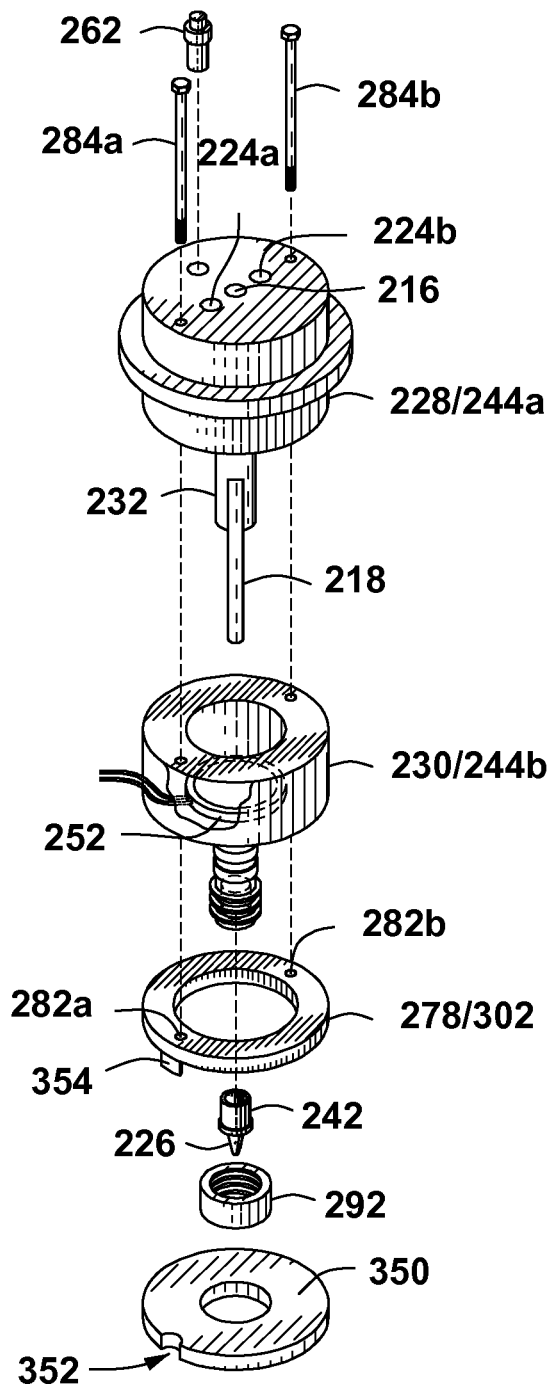
FIG. 21 illustrates an embodiment of a nozzle assembly.

FIG. 21 illustrates an exploded view of the nozzle assembly (210). Such a nozzle assembly (210). The exploded view illustrates a first fastener (284a) and a second fastener (284b) for securing a first nozzle piece (244a), in the form of a nozzle cap (228), and a second nozzle piece (244b), in the form of a nozzle base (230), to a nozzle seat (302). The nozzle assembly (210) may, however, be constructed with any number of fasteners (284) and nozzle pieces (244). In the illustrated embodiment, the nozzle seat (302) includes a first threaded portion (282a) for receiving the first fastener (284a) and a second threaded portion (282b) for receiving the second fastener (284b). In other embodiments the fasteners may be combined with and/or omitted in favor of adhesives, or other coupling means such as magnets or mechanical means including springs.

The nozzle cap (228) may include a sample inlet (216) which is in fluid communication with an injection stem (232) and an injection tube (218) for forming a fluid flow path. The injection stem (232) may be integrally formed with the nozzle cap (228), or they may be formed as separate nozzle piece. The injection tube (218) may be over molded, or inset molded, with the nozzle cap (228) in a manner which provides fluid communication between the sample inlet (216) and the injection tube (218). This technique can provide for a very short and precisely located injection tube (218). In one embodiment a device may be coupled to the stem (232) which provides a surface with an adjustable axial position. As one example, the injection tube (218) may be over molded onto such an element, which is then mechanically coupled to the injection stem (232). In one embodiment, the injection tube (218) is formed from a smooth rigid material to ensure desired fluid flow properties. In an alternative embodiment, the injection tube is formed from a more pliable material, which may be manipulated after the injection tube is formed or molded. For example, the injection tube may be manipulated to change the initial geometry of a fluid path formed there through for the purpose of encourage a ribbon core stream. As a non-limiting example, modifications to the geometry may be incorporated by laser etching certain portions or by a manufacturing step of squeezing the injection tube while in pliable, and not perfectly elastic state. Other manufacturing techniques may also be incorporated to shape the outlet of the injection tube, such that one axis is longer than a second axis. As but an illustrative example, other manufacturing techniques may be employed resulting in an elliptical or rectangular injection tube outlet.

The second nozzle piece (244b), in the form of a nozzle base (230), may be dimensioned for coupling with the nozzle cap (228). An oscillating element (252) may be insert molded with the nozzle base (230), or may be potted into a cavity in the nozzle base (230). In one embodiment the nozzle base (230) is dimensioned to receive a nozzle tip (242). For example, the nozzle base (230) may include interior dimensions for coupling with the nozzle tip (242), while the exterior of the nozzle base may be threaded for receiving a retaining nut (292) that holds the nozzle tip (242) in place. In another embodiment, the nozzle tip (242) may be insert molded with nozzle base (230), and in yet another embodiment the nozzle tip may be molded as a portion of the nozzle base (230).

The nozzle seat (302) may take the form of a nozzle clamp (278) which receives the first fastener (284a) and the second fastener (284b) in a manner which clamps the nozzle cap (228) to the nozzle base (230). The nozzle seat (302) may be dimensioned for fastener free coupling to the receiver (350). As one example, the nozzle seat (302) can comprise a metallic material coupled to a receiver (350) having magnetic properties. A magnetic material may be located on either one of or both of the nozzle seat (302) and the receiver (350). In a similar embodiment, one or both of these components may be constructed to include electromagnets, or materials which demonstrate magnetic properties in response to electric current. In this configuration, a nozzle assembly (210) may be simply dropped into place and held by gravity and the coupling of magnetic components. Such nozzles are quickly and easily interchangeable. In many environments flow cytometer down time results in lost production time and nozzles seat (302) as described herein provide an extremely efficient method of replacing nozzles and may improve the productivity of a given flow cytometer system. The nozzle seat (302) and receiver (350) may be constructed in a variety of other configuration for coupling the nozzle to a flow cytometer in a fastener free manner. In one embodiment the nozzle seat (302), or the receiver (350), may include springs for securing the two pieces in a fastener free engagement. For example, a spring loaded ball on one component may be designed to lock into socket on the other component. The nozzle seat (302) may also be physically dimensioned for an interlocking configuration with a seat on an adjustable stage at the flow cytometer head. In such an embodiment, the nozzle seat (302) may be so dimensioned for being received by an adjustable stage. Once in place, the nozzle seat (302) may be secured by rotation to achieve an interlocking assembly, or by other mechanical means, such as mechanical means provided on the adjustable stage.

The nozzle seat (302) may include an alignment element (354) in the form of a protrusion which generally extends past a remaining boundary of the bottom surface of the nozzle seat (302). The receiver (350) may include an alignment notch (352). The alignment element (354) and alignment notch (352) may be so dimensioned to favor coupling in specified orientation. In other embodiments, there may be a plurality of alignment notches (352) for potentially securing a single alignment element (354). In this configuration, the nozzle assembly (210) may rest in one of a plurality of predefined orientations relative to the flow cytometer system. In another embodiment, the receiver (350) is adjustable and may be secured in a plurality of positions for modifying the orientation provided by aligning the alignment element (354) and the alignment notch (352). In one embodiment, a spring loaded ball may serve as both a means for engaging the nozzle seat (302) with the receiver (305) and as the alignment element (354) for aligning the two components. While additional components of the flow cytometer have not been illustrated, it should be understood that the receiver (350) may be firmly attached to a stage, such as a stage which is adjustable in two or three dimensions for alignment purposes.

The alignment element (354) and the alignment notch (352), in addition to providing a specified orientation, may provide a precise nozzle location allowing the rapid replacement of a nozzle assembly and minimizing the need for realigning the flow cytometer. In combination with the magnetic coupling, this configuration may eliminate forces which tend to bring the nozzle out of alignment with the detectors or source of electromagnetic radiation. Specifically, torque may be applied to the adjustable stage on which the nozzle sits when fasteners are secured into place by the downward force an operator applies to the fasteners themselves.

Grooves, slots, and other matched surfaces and geometries may also be used, alone, or in combination with magnetic coupling, to provide additional configurations which allow the quick and precise matching to a preferred orientation and/or location. In another embodiment, visual aids in the form of marks or notches may be applied to the nozzle to facilitate the quick and easy replacement of nozzles.

As can be understood from the foregoing, the basic concepts of the present invention may be embodied in a variety of ways. As such, the particular embodiments or elements of the invention disclosed by the description or shown in the figures accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Moreover, for the purposes of the present invention, the term "a" or "an" entity refers to one or more of that entity; for example, "a nozzle" refers to one or more of the nozzles. As such, the terms "a" or "an", "one or more" and "at least one" can be used interchangeably herein.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A flow cytometer system comprising:
a nozzle assembly for producing a fluid stream with particles, the nozzle assembly comprising an orienting nozzle tip formed from a cylindrical body defining a longitudinal axis and a frustoconical body adjoining the cylindrical body on the longitudinal axis which is in fluid communication with the cylindrical body, wherein the frustoconical body ends in a flat surface transverse to the longitudinal axis which has a nozzle exit orifice, and wherein the frustoconical body further comprises a cutout at the edge of the flat surface and the frustoconical body, the frustoconical body further comprising an exterior surface having a proximal portion and a distal portion, wherein the proximal portion of the frustoconical body has a first angle of taper and wherein the distal portion of the frustoconical body has a second angle of taper, and wherein the second angle of taper is greater than the first angle of taper;
a source of electromagnetic radiation for producing a beam incident upon the fluid stream and the particles; and
a detector for detecting light emitted or reflected from the particles within the fluid stream in response to the beam.

2. The flow cytometer of claim 1, wherein the orienting nozzle tip comprises an interior surface.

3. The flow cytometer of claim 1, wherein the interior surface of the orienting nozzle tip comprises an orienting geometry.

4. The flow cytometer of claim 3, wherein the interior surface of the orienting nozzle tip transitions from a circular cross section to an elliptical cross section then to a circular exit orifice.

5. The flow cytometer of claim 1, wherein the cutout comprises a chamfer.

6. The flow cytometer of claim 1, wherein the cutout comprises a groove.

7. The flow cytometer of claim 1, further comprising a notch formed in the cylindrical body for positioning the nozzle tip within a nozzle assembly of a flow cytometer.

8. The flow cytometer of claim 1, wherein the cutout comprises a chamfer and wherein the angle of the chamfer is about the same as an expected vertical angle of emissions produced by particles in the fluid stream in response to the beam.

9. The flow cytometer of claim 8, wherein the angle of the chamfer in the chamfered nozzle tip is between 15 and 60 degrees.

10. The flow cytometer of claim 9, wherein the angle of the chamfer in the chamfered nozzle tip is about 30 degrees.

11. The flow cytometer of claim 1 wherein the nozzle assembly further comprises:
a nozzle assembly;
a sample inlet in fluid communication with an injection tube having a sample outlet, the injection tube being mounted with the nozzle assembly and extending along the interior of the nozzle assembly;
one or more sheath inlets in fluid communication with the nozzle assembly; and wherein the nozzle exit orifice is downstream of the sample outlet.

12. The flow cytometer of claim 1, wherein the beam produced the source of electromagnetic radiation is focused on the fluid stream within 300 micrometers of the exit orifice.

13. The flow cytometer of claim 1, further comprising a sorting mechanism.

14. The flow cytometer of claim 13, wherein the sorting mechanism comprises an oscillator in communication with the fluid stream for producing droplets, a charge pin in communication with the fluid stream for charging droplets as they form and deflection plates to deflect charged droplets.

15. A nozzle tip comprising:
a cylindrical body defining a longitudinal axis;
a frustoconical body adjoining the cylindrical body on the longitudinal axis and in fluid communication with the cylindrical body, wherein the frustoconical body ends in a flat surface transverse to the longitudinal axis which has a nozzle exit orifice, and wherein the frustoconical body further comprises a cutout at the edge of the flat surface and the frustoconical body, the frustoconical further comprising an exterior surface having a proximal portion and a distal portion, wherein the proximal portion of the frustoconical body has a first angle of taper and wherein the distal portion of the frustoconical body has a second angle of taper, and wherein the second angle of taper is greater than the first angle of taper; and
an interior surface having an orienting geometry.

16. The nozzle tip of claim 15, wherein the cutout comprises a chamfer.

17. The nozzle tip of claim 15, wherein the cutout comprises a groove.

18. The nozzle tip of claim 15, wherein the nozzle tip comprises an orienting nozzle tip.

19. The nozzle tip of claim 15, wherein the interior surface of the nozzle tip transitions from a circular cross section to an elliptical cross section then to a circular exit orifice.

20. The nozzle tip of claim 15, further comprising a notch formed in the cylindrical body for positioning the nozzle tip within a nozzle assembly of a flow cytometer.

21. The nozzle tip of claim 15, wherein the cutout comprises a chamfer and wherein the angle of the chamfer is about the same as the expected vertical angle of emissions produced by particles in the fluid stream in response to the beam.

22. The nozzle tip of claim 15, wherein the angle of the chamfer in the chamfered nozzle tip is between 15 and 60 degrees.

23. The nozzle tip of claim 15, wherein the angle of the chamfer in the chamfered nozzle tip is about 30 degrees.

* * * * *